(12) United States Patent
Jarling (10) Patent No.: US 9,381,336 B2
(45) Date of Patent: Jul. 5, 2016

(54) DEVICE FOR REPEATED PIERCING OF SKIN, AND PIERCING MODULE

(75) Inventor: Christian Reinhold Jarling, Berlin (DE)

(73) Assignee: MT.DERM GMBH, Berlin (DE)

( * ) Notice: Subject to any disclaimer, the term of this patent is extended or adjusted under 35 U.S.C. 154(b) by 1183 days.

(21) Appl. No.: 13/323,597

(22) Filed: Dec. 12, 2011

(65) Prior Publication Data

US 2012/0158032 A1 Jun. 21, 2012

(30) Foreign Application Priority Data

Dec. 10, 2010 (DE) .................... 20 2010 013 095 U (51) Int. Cl.
*A61B 17/34* (2006.01)
*A61M 37/00* (2006.01)

(52) U.S. Cl.
CPC ........... *A61M 37/00* (2013.01); *A61M 37/0076* (2013.01)

(58) Field of Classification Search
CPC .......................... A61M 37/00; A61M 37/0076
USPC ............ 606/185, 186, 84, 116, 189; 600/564, 600/568; 30/358; 81/9.22; 452/141, 144, 452/146; 101/26, 30
See application file for complete search history.

(56) References Cited

U.S. PATENT DOCUMENTS

| | | | |
|---|---|---|---|
| 2,551,902 A * | 5/1951 | Rieck ............................. | 604/173 |
| 2,593,110 A * | 4/1952 | Crane et al. ................... | 606/116 |
| 5,697,901 A | 12/1997 | Eriksson | |
| 6,743,211 B1 * | 6/2004 | Prausnitz et al. ............. | 604/239 |
| 8,551,098 B2 * | 10/2013 | Shimko et al. ................. | 606/84 |
| 2002/0123675 A1 | 9/2002 | Trautman et al. | |
| 2004/0058882 A1 | 3/2004 | Erikksson et al. | |
| 2004/0116953 A1 * | 6/2004 | Dixon ........................... | 606/186 |
| 2007/0149991 A1 * | 6/2007 | Mulholland .................. | 606/186 |
| 2008/0009811 A1 * | 1/2008 | Cantor .......................... | 604/272 |
| 2008/0306502 A1 | 12/2008 | Lisec | |

(Continued)

FOREIGN PATENT DOCUMENTS

| | | |
|---|---|---|
| DE | 202004010659 U1 | 10/2004 |
| DE | 102004032892 A1 | 2/2006 |

(Continued)

OTHER PUBLICATIONS

Machine Translation of DE202004010659, date translated Aug. 11, 2015, pp. 1-7.*

(Continued)

*Primary Examiner* — Jing Ou
(74) *Attorney, Agent, or Firm* — Leason Ellis LLP (57) ABSTRACT

The application relates to a device for repeated puncturing of the skin, with a housing, a drive device, which is accommodated in the housing and configured to provide a driving force, a coupling mechanism, which is accommodated in the housing, and a piercing device, which via the coupling mechanism driving force for a repetitive piercing movement is coupled to the piercing device, and the piercing device includes a base having a thereto formed distal active area, over which a plurality of spaced piercing elements are distributed, and where the base with the thereto formed distal active surface is mounted relative to the housing can be tilted. Furthermore, the application relates to a piercing module for a device for repeated puncturing of the skin.

17 Claims, 5 Drawing Sheets

(56) References Cited

U.S. PATENT DOCUMENTS

2011/0092884 A1* 4/2011 Kang .............................. 604/21
2012/0041374 A1* 2/2012 Lee ................................ 604/173

FOREIGN PATENT DOCUMENTS

| DE | 102008010890 A1 | 8/2009 |
| EP | 1958659 A1 | 8/2008 |
| KR | 100922138 B1 | 10/2009 |
| WO | 2007015232 A1 | 2/2007 |
| WO | WO 2010/070619 * 6/2010 | ............ A61M 37/00 |
| WO | 2010120111 A2 | 10/2010 |

OTHER PUBLICATIONS

European Search Report, directed to EP11172089, mailed on Sep. 28, 2011, 5 pages.

* cited by examiner

DEVICE FOR REPEATED PIERCING OF SKIN, AND PIERCING MODULE

BACKGROUND OF THE INVENTION

Devices for repeated piercing of skin are used in order to pierce human or animal skin locally in the region of the layers near the surface. Such means, for example, can be used to introduce substances into the skin, for example cosmetic or medical materials. In similar manner, local piercing of skin is employed in order to apply a dye for tattooing or to apply permanent makeup.

Devices for repeated piercing of skin, usually constructed as hand-held tools, are known in embodiments wherein a drive device, for example an electric motor, is used to provide the power for repetitive piercing. The power provided by the drive device is supplied via a coupling mechanism to a piercing device which is moved to and fro in order to pierce the skin locally. Examples of piercing devices that may be used are single needles or groups of needles. These latter are of particular application in tattooing devices.

Furthermore, it has been suggested that so-called needle plates be used for the piercing devices. To this end, the piercing device has a needle plate with a plurality of separated piercing elements distributed over it. The piercing elements are formed as needle or knife points, for example. In this connection, document DE 20 2004 010 659 U1 discloses a device for perforating skin wherein a needle plate is repetitively moved to and fro with the aid of a drive device. The needle plate in that case is guided in a needle plate guide device. The needle plate guide device acts to determine the penetration of the needles into the skin, whereby the needle plate guide device at the sides of the needle plate provides a circumferential guide. The needle plate guide device thus prevents tilting of the needle plate during the repetitive piercing motion.

In addition, document US 2004/005882 A1 discloses a device for piercing skin wherein the needles are arranged on a base in rows, whereupon the base is guided on an associated housing portion when the repetitive piercing movement is carried out.

A method and a device for local piercing of skin by means of a needle plate are also known from document US 2002/0123675 A1.

A device for locally piercing skin is also known from document U.S. Pat. No. 5,697,901.

SUMMARY OF THE INVENTION

The aim of the invention is to provide a device for repeated piercing of skin as well as a piercing module with which local skin piercing is optimized.

This aim is achieved in accordance with the invention by means of a device for repeated piercing of skin in accordance with the independent claim 1. A piercing module according to independent claim 15 is also provided. The subject matter of the dependent claims defines advantageous embodiments of the invention.

The invention embodies the concept of a device for repeated piercing of skin, having a housing, a drive device, which is accommodated in the housing and configured to provide power, a coupling mechanism, which is accommodated in the housing, and a piercing device which couples to the drive device via the coupling mechanism in a manner such that the power for a repetitive piercing movement is coupled to the piercing device by means of the coupling mechanism, wherein the piercing device has a base having a distal working head formed thereon over which a plurality of separated piercing elements are distributed, and wherein the base with the distal working head formed thereon is tiltably mounted with respect to the housing.

In addition, a piercing module is provided for such a device, having a housing portion and a piercing device which couples to a coupling mechanism portion, wherein the piercing device has a base having a distal working head formed thereon over which a plurality of separated piercing elements are distributed, and wherein the base with the distal working head formed thereon is tiltably mounted with respect to the housing portion.

Because of the invention, the base with the distal or frontal working head formed thereon is tiltably mounted with respect to the housing, which allows the working head with the piercing elements formed thereon to align itself with respect to the skin surface during the skin piercing procedure, in particular when the housing of the device is not applied to the skin surface in a perpendicular manner. The guides provided for needle plates disclosed in the prior art prevent the position of the needle plate from being aligned by tilting in just such a manner. IN summary, it is easier for the operator of the device for piercing skin to handle it since local piercing of the skin always occurs in an optimized manner even when the housing of the device and thus the straight path of movement of the shaft of the piercing device is tilted by the operator, i.e. it is not perpendicular to the skin surface, when guiding the device to and fro over the skin surface.

A variety of embodiments can be envisaged for the piercing elements arranged on the surface of the head. Thus, knives and/or needles or even knife points and/or needle points may be formed. The needles or needle points may have a conical shape. In one embodiment, the piercing elements may be arranged on the surface of the working head in one or more rows which may be circumferential. The surface of the working head itself may have any basic shape, for example circular, oval or angular. In one embodiment, the piercing elements may essentially be evenly distributed over the working head. Alternatively, the piercing elements may be distributed along the circumferential rim of the working head, whereas a central region is completely free of piercing elements or may have a lower distribution density for the piercing elements than in the rim region.

In a further preferred embodiment of the invention, the tiltable mount for the base has a tilt limiter. In one embodiment, the tilt limiter may be formed as a single- or multi-sided stop. In one embodiment, with the tilt limiter, the possible tilt of the base with the distal working head formed thereon is limited to a tilt angle of at most approximately 20°, preferably at most approximately 10° and more preferably at most approximately 5°. It is also possible for the tilt angle to be different in different tilt directions.

In an advantageous embodiment of the invention, the tiltable mount for the base is formed with a ball joint mount. In this embodiment or in connection with other mounting mechanisms, the base may be detachably coupled to the coupling mechanism. In a further embodiment, base elements with different shapes can be coupled in this manner; as an example, they may differ in shape and/or size of the working head and/or as regards the construction of the piercing elements. Alternatively, a universal joint coupling may be provided.

In an advantageous embodiment of the invention, the base is also mounted so that it does not come into contact with the housing even in the tilted position. In this embodiment, not only does the base not come into contact with the housing in the non-tilted position, but also it does not come into contact in any of the possible tilted positions.

In a refinement of the invention, in at least a retracted position the distal working head is preferably arranged behind an associated housing opening within the housing. This means that the working head is arranged behind the surface of the associated housing opening. In a preferred embodiment, the piercing elements are preferably also entirely retracted behind the surface of the associated housing opening in the retracted position. Thus, for example, risk of injury is reduced.

In an advantageous embodiment of the invention, in a deployed position, the distal working head is arranged in the plane of the surface of the associated housing opening. Arranging the distal working head in the surface of the associated housing opening means that the separated piercing elements project beyond the surface of the associated housing opening. If the distal working head is tilted in the deployed position of the base, this means that the surface of the associated housing opening and the distal working head are tilted towards each other. Alternatively, in the deployed position the distal working head may be arranged so that it is still behind the surface of the associated housing, opening or it may be positioned in front of it.

In a further embodiment of the invention, upon displacement between the retracted and the deployed position in the context of the repetitive piercing movement, the distal working head may be substantially in an enclosed region of the housing. In this embodiment, over more than 50% of the stroke length of the repetitive piercing movement, the base moves in a region which is encompassed by the housing.

In a further preferred embodiment of the invention, in the region of the distal working head, through-openings are arranged which are formed either integral with the piercing elements and/or separately therefrom. In one embodiment, the through-openings enable a substance to be introduced into the skin surface to be supplied to the piercing locations; in this case, they form supply openings. Alternatively or supplementally, at least a portion of the through-openings may be formed as exhaust openings by means of which liquid can be discharged rearwardly from the region between the skin surface and the working head. In this manner, for example, a liquid film is prevented from building up between the skin surface and the working head, which film would prevent or hinder the piercing process. In addition, an arrangement of supply/exhaust openings may be envisaged, i.e. through-openings which carry out a combined function. The through-openings may, for example, be formed in the piercing elements themselves, whereupon they may be formed as hollow needles, for example. Alternatively or supplementally, through-openings may be provided separately from the piercing elements in the base. In one embodiment, the through-openings have a diameter of approximately 0.3 to approximately 0.5 mm, preferably approximately 0.4 mm.

In an advantageous embodiment of the invention, the distal working head is convexly curved. The convex shape of the distal working head may have a two-dimensional or three-dimensional form, whereupon the latter may be in the shape of a section of a spherical surface.

In an advantageous embodiment of the invention, the base is coupled to a distal end of a shaft element comprised in the coupling mechanism, wherein the shaft element runs in a shaft guide. The shaft guide comprises a bushing, for example. In a further embodiment, the shaft element may be accommodated in the shaft guide in a twist-proof manner. As an example, a mechanical twist guard may be provided. Alternatively or supplementally, unintentional twisting of the shaft element during the repetitive piercing movement may be prevented by means of a magnetic twist guard.

Preferably, in a refinement of the invention, a proximal end of the shaft element is guided through a membrane opening. With the aid of the membrane formed from elastic material, a frontal section of the housing is sealed off so that liquid residues in particular cannot gain ingress into the drive device, even when the shaft element is moved to and fro. In one embodiment, with the aid of the membrane, which may be U-shaped or cup-shaped, for example, a restoring or return force is produced for the shaft element and thus for the piercing device. This restoring force can be a supplement or stand alone to allow the piercing device to return to the retracted position. If the device is constructed in a modular manner, then the membrane formed from elastic material can seal the back of the piercing module.

In an advantageous embodiment of the invention, an additional element may be provided on the shaft element, encompassing it. In one embodiment, the additional element is arranged between the shaft guide and the elastic membrane on the shaft element. In this embodiment, the back of the shaft guide, i.e. on a side facing the additional element, may have a recess for the additional element. In a yet still further embodiment, a projection is provided on the shaft element, which prevents unintentional shifting of the additional element on the shaft element. The additional element may be formed as a wiping and/or attenuating element.

In a further embodiment of the invention, a frontal housing section may be detachably arranged on the housing. In one embodiment, the base of the piercing device is accommodated in the frontal housing section. An inner surface in the frontal housing section may be concave in shape. Such an embodiment is possible both in the embodiment with a releasable housing section and that with the non-releasable housing section.

In an advantageous embodiment of the invention, the housing may be formed from a plurality of modules, each with an associated housing portion, which are detachably connected together, wherein the plurality of modules comprise a drive module with the drive device and a piercing module in which at least the shaft element and the base coupled thereto are accommodated. The piercing module may be in the form of a sterile disposable module.

DESCRIPTION OF PREFERRED EMBODIMENTS OF THE INVENTION

The invention will now be described in more detail with the aid of preferred embodiments made with reference to the figures of the drawing, in which.

Figure 1:
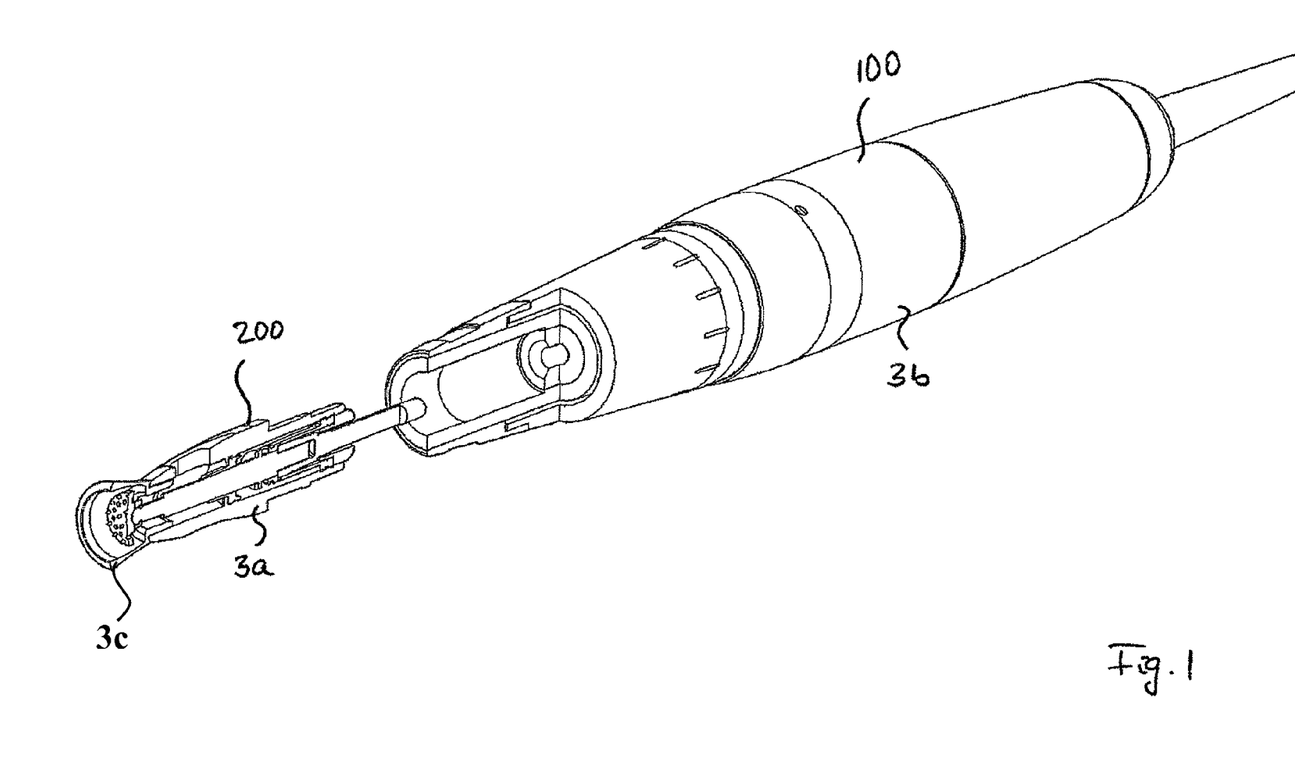
FIG. 1 is a diagrammatic sectional view in part elevation of a device for repeated piercing of skin with a drive module and a piercing module coupled thereto.

FIG. 1 shows a diagrammatic sectional view of a device for repeated piercing of skin with a drive module 100 and a piercing module 200 coupled thereto. In the view shown, the piercing module 200 is detached from the drive module 100.

In the device for piercing skin in its usual form of a hand tool, the piercing module 200 couples to the end of the drive module 100 which comprises a drive device for providing power, for example an electric motor. Such drive modules are known per se in a variety of embodiments and thus will not be described here in any further detail.

Figure 2:
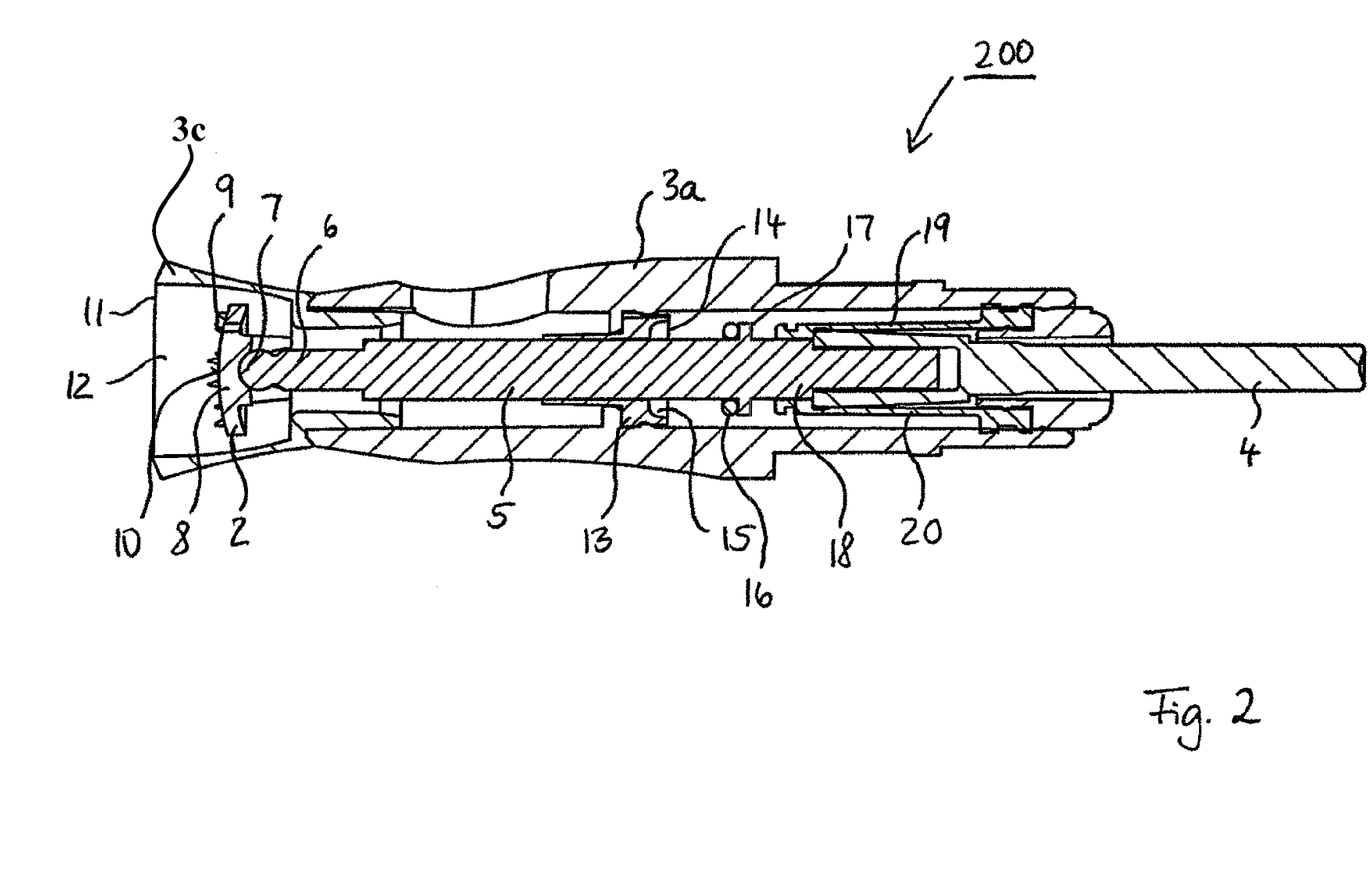
FIG. 2 is a diagrammatic sectional view of the piercing module for the device of FIG. 1.

FIG. 2 shows a sectional view of the piercing module 200. A coupling mechanism which is formed partly in the drive module 100 and partly in the piercing module 200 serves to introduce the power produced by the drive device into a piercing device 2 so that this latter executes a repetitive to and fro movement. FIG. 2 shows the piercing device 2 in a retracted position.

In the views of FIGS. 1 and 2, the piercing device 2 is arranged in a housing portion 3a associated with the piercing module 200; together with a housing portion 3b associated with the drive module 100, it forms a housing of the device.

For the coupling mechanism, FIG. 2 shows an extension 4 and a shaft element 5 which is inserted into the extension 4. At the distal end 6 of the shaft element 5, the piercing device 2 is coupled to the shaft element 5 with the aid of a ball joint mount 7. The ball joint mount 7 allows a base 8 of the piercing device 2 to take up different tilted positions, both in the retracted position shown in FIG. 2 and in the deployed position (not shown) in which at least piercing elements 9, which are arranged on a working head 10 of the base 8 of the piercing device 2, are arranged in front of a surface 11 of an opening 12 in the housing associated with the piercing device 2, so that the human or animal skin can be pierced. The working head 10 arranged on the base 8 which is distal to the shaft element 5 is convex in shape. In the region behind the housing opening 12, the inner housing surface opposite the base 8 is concave, facilitating free tilting of the base 8 on the ball joint mount 7.

Upon repetitive to and fro movement, the shaft element 5 slides in a shaft guide 13 which is shaped as a bushing, by means of which the shaft element 5 is also prevented from unintentional twisting about its longitudinal axis. To this end, in this embodiment, twist-proofing is achieved by means of the shaft guide 13. On a rear side 14, the shaft guide 13 has a circumferential recess 15 for an additional element 16 formed as a wiping/attenuating element, which in the embodiment shown is formed as an O-ring. In the embodiment shown in FIG. 2, the additional element 16 is supported on a projection 17 which delimits the back of the region of the shaft element 5 to which the additional element 16 has access.

A proximal end 18 of the shaft element 5 is surrounded by a membrane 19 formed from elastic material. With the aid of the membrane 19, the space in front of the membrane 19 in the housing portion 3a of the piercing module 200 is sealed off. When the piercing device 2 is displaced into the deployed position by applying the power, lateral sections 20 of the membrane 19 are stretched, whereupon a restoring or return force acts on the extension 4 and the shaft element 5.

Figure 3:
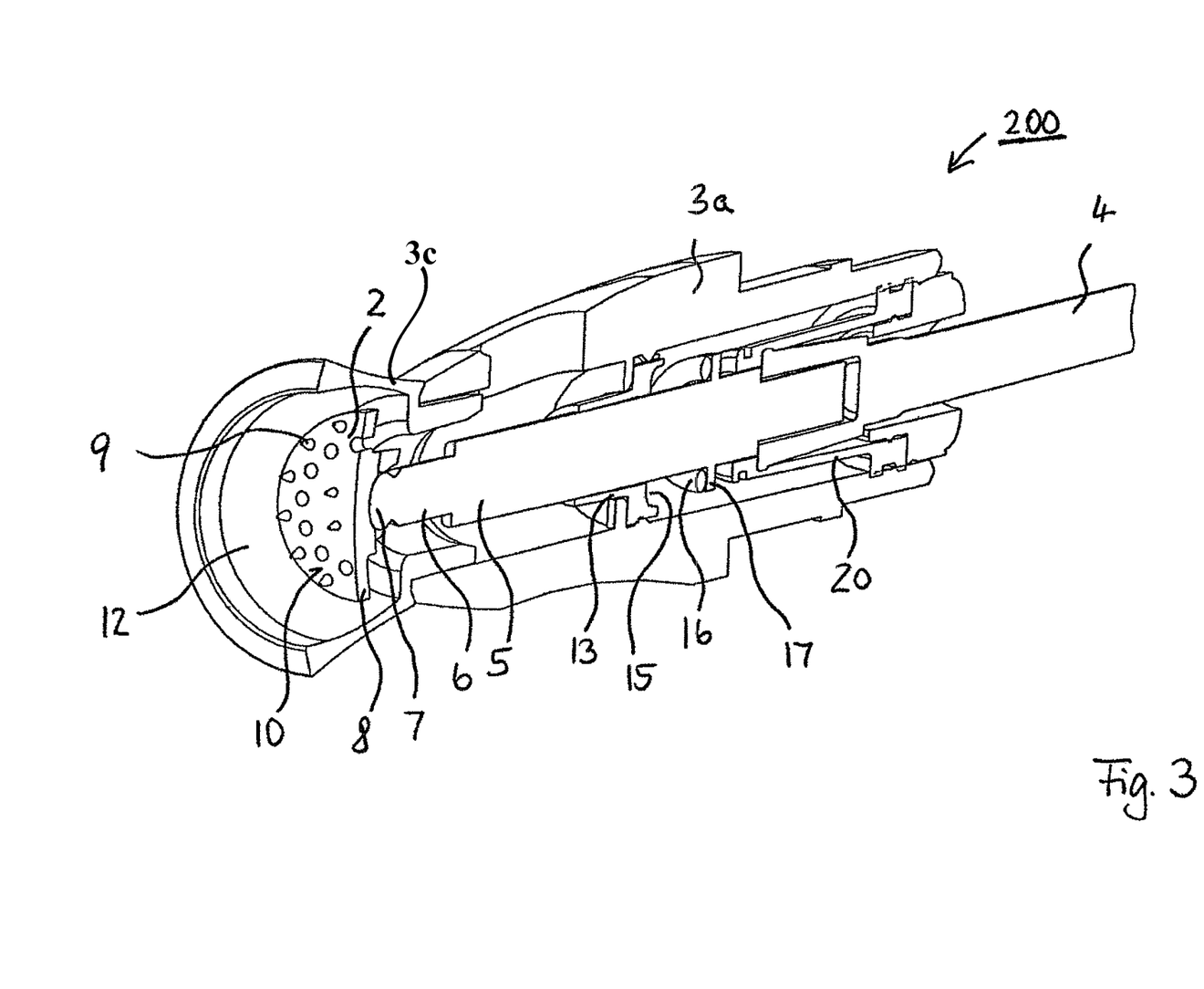
FIG. 3 is a perspective sectional view of the piercing module from FIG. 2.

FIG. 3 shows a perspective sectional view of the piercing module 200 from FIG. 2.

Figure 4:
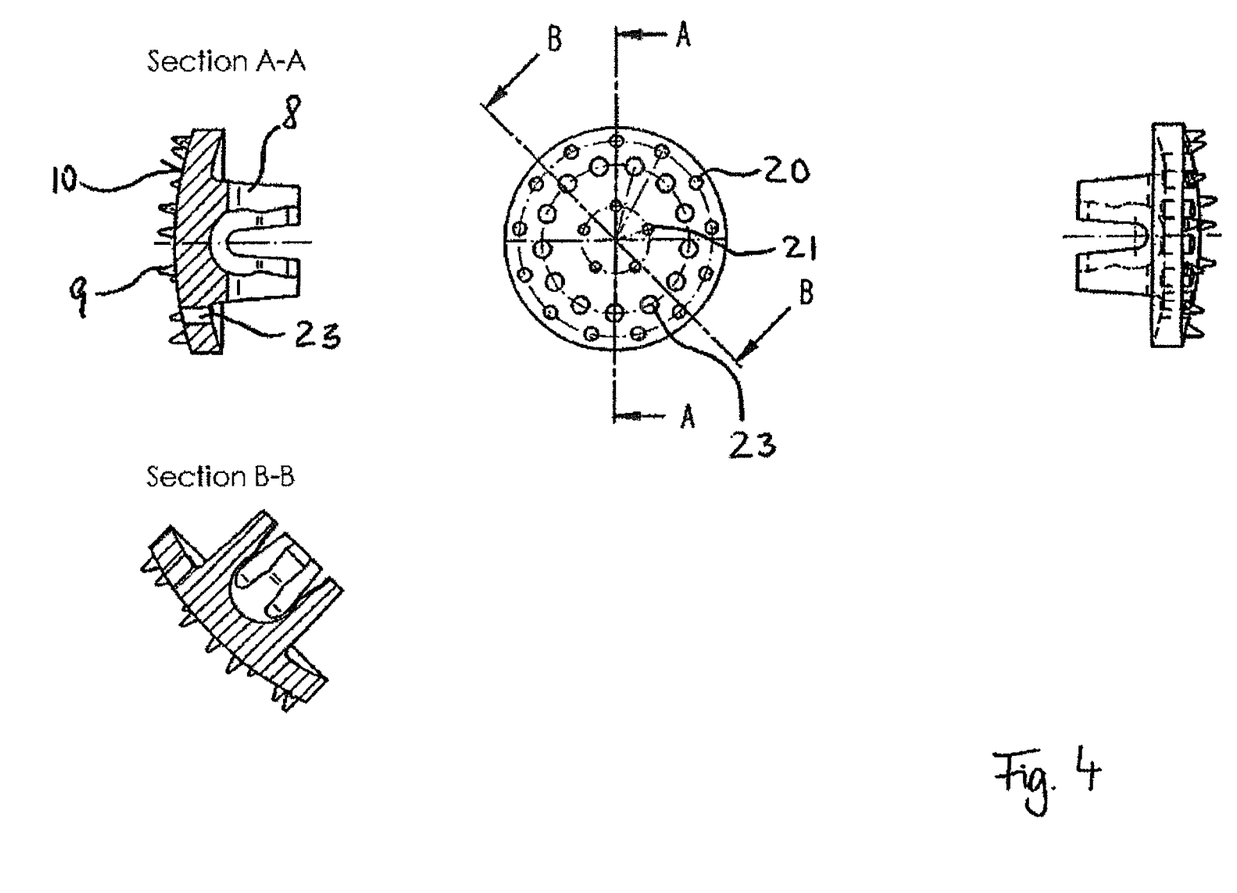
FIG. 4 is a diagrammatic view of a base for a piercing device.

FIG. 4 shows diagrammatic views of the base 8 of the piercing device 2. The piercing elements 9, which may be knife or needle points, are distributed evenly along both an outer ring 21 and an inner ring 22, i.e. with identical distances between neighbours on both sides. Through-openings 23 are formed between the outer ring 21 and the inner ring 22.

Figure 5:
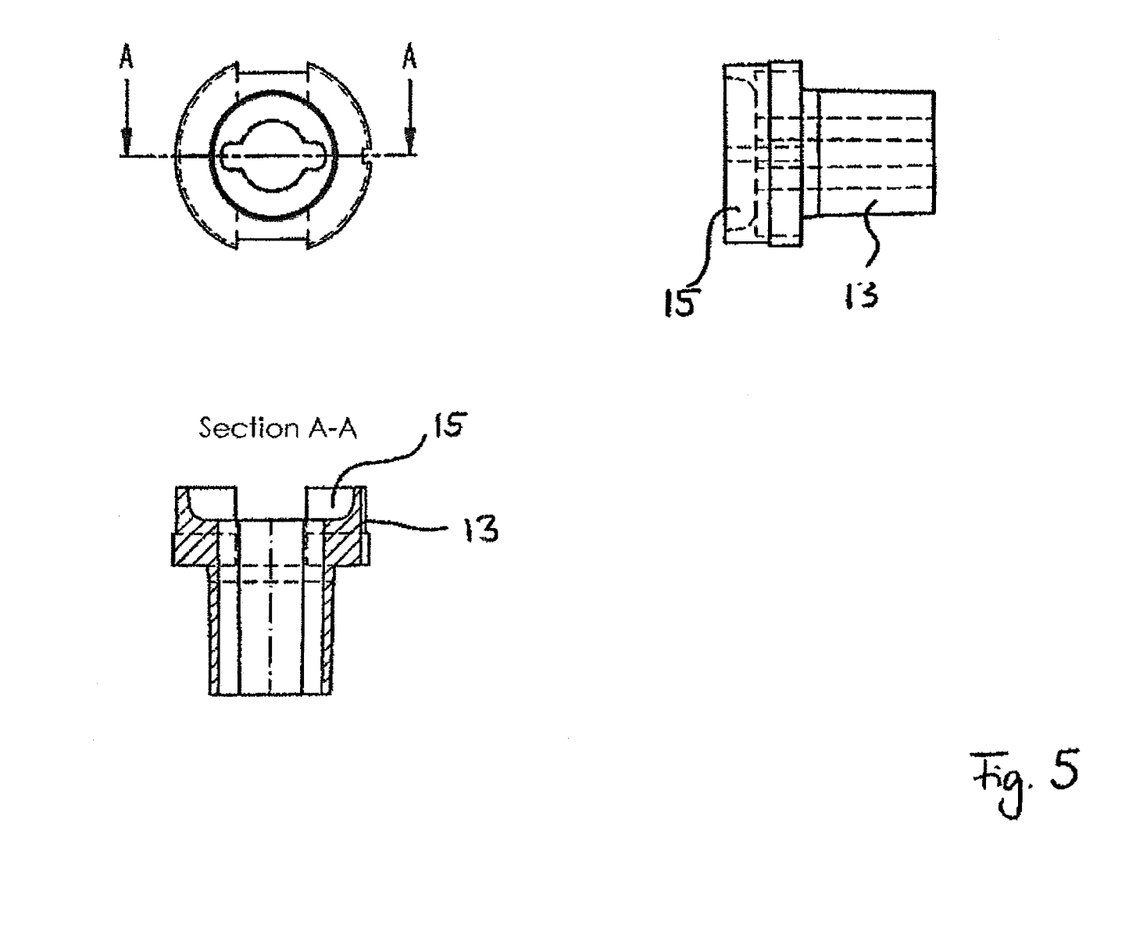
FIG. 5 is a diagrammatic view of a shaft element guide.

FIG. 5 shows a diagrammatic view of the shaft guide 13.

The features of the invention disclosed in the above description, claims and drawing may be used in any combination to embody the invention in its various embodiments.

The text of German priority application no. DE 202010013095 filed Dec. 10, 2010 is hereby incorporated by reference.

The invention claimed is:

1. A device for repeated piercing of skin, having:
a housing having a distal housing opening;
a drive device which is accommodated in the housing and configured to provide power;
a coupling mechanism which is accommodated in the housing;
a piercing device which couples to the drive device via the coupling mechanism in a manner such that the power for a repetitive piercing movement is coupled to the piercing device by means of the coupling mechanism;
wherein the piercing device has a base having a distal working head formed thereon over which a plurality of separated piercing elements are distributed, and
a tiltable mount, wherein the base with the distal working head formed thereon is tiltably mounted with respect to the housing by the tiltable mount, wherein the base with the distal working head is tiltable with respect to the housing including while the distal working head is arranged inside the housing behind the distal housing opening.

2. The device as claimed in claim 1, wherein the tiltable mount for the base has a tilt limiter.

3. The device as claimed in claim 1, wherein the tiltable mount for the base is formed by a ball joint mount.

4. The device as claimed in claim 1, wherein in a deployed position, the distal working head is arranged in a plane of a surface of the distal housing opening.

5. The device as claimed in claim 1, wherein upon displacement between a retracted position and a deployed position in the context of a repetitive piercing movement, the distal working head moves substantially in an enclosed region of the housing.

6. The device as claimed in claim 1, wherein, in a region of the distal working head, through-openings are arranged which are formed integral with the piercing elements and/or are formed separately thereof.

7. The device as claimed in claim 1, wherein the distal working head is convexly curved.

8. The device as claimed in claim 1, wherein the base is coupled to a distal end of a shaft element comprised in the coupling mechanism, wherein the shaft element runs in a shaft guide.

9. The device as claimed in claim 8, wherein a proximal end of the shaft element is guided through a membrane opening.

10. The device as claimed in claim 8, further comprising an additional element arranged on the shaft element, encompassing it.

11. The device as claimed in claim 1, further comprising a frontal housing section is detachably arranged on the housing.

12. The device as claimed in claim 1, wherein the housing is formed from a plurality of modules each with an associated housing portion which are detachably connected together, wherein the plurality of modules comprise a drive module with the drive device and a piercing module with the piercing device.

13. A device for repeated piercing of skin, having:
a housing having a distal housing opening;
a drive device which is accommodated in the housing and configured to provide power;
a coupling mechanism which is accommodated in the housing; and
a piercing device which couples to the drive device via the coupling mechanism in a manner such that the power for a repetitive piercing movement is coupled to the piercing device by means of the coupling mechanism;

wherein the piercing device has a base having a distal working head formed thereon over which a plurality of separated piercing elements are distributed, and wherein the base is mounted with respect to the housing such that even in a tilted position, it does not come into contact with the housing, wherein the base with the distal working head is tiltable with respect to the housing including while the distal working head is arranged inside the housing behind the distal housing opening.

14. The device as claimed in claim 13, further comprising a tiltable mount, wherein the base with the distal working head formed thereon is tiltably mounted with respect to the housing by the tiltable mount.

15. The device as claimed in claim 14, wherein the tiltable mount further comprises a tilt limiter.

16. The device as claimed in claim 13, wherein, upon displacement between a retracted position and a deployed position in the context of a repetitive piercing movement, the distal working head moves substantially in an enclosed region of the housing.

17. The device as claimed in claim 13, wherein the base is coupled to a distal end of a shaft element comprised in the coupling mechanism, wherein the shaft element runs in a shaft guide and wherein a proximal end of the shaft element is guided through a membrane opening.

* * * * *